United States Patent [19]

Eusek et al.

[11] Patent Number: 4,665,543
[45] Date of Patent: May 12, 1987

[54] METHOD AND APPARATUS FOR ESWL IN-BATH FILMING

[75] Inventors: John F. Eusek, Woodinville; William H. Bush, Seattle, both of Wash.

[73] Assignee: The Mason Clinic, Seattle, Wash.

[21] Appl. No.: 813,394

[22] Filed: Dec. 23, 1985

[51] Int. Cl.$^4$ .................. A61B 8/12; G03B 12/02; G03B 12/06

[52] U.S. Cl. ................................ 378/181; 128/328; 378/190

[58] Field of Search ............... 378/189, 190, 181, 177, 378/180, 51, 58, 59, 34, 182; 128/328, 660, 665; 250/256, 268; 354/64

[56] References Cited

U.S. PATENT DOCUMENTS

| | | |
|---|---|---|
| 2,619,599 | 11/1952 | Smith . |
| 2,962,591 | 11/1960 | McNabb, Jr. et al. . |
| 3,214,586 | 10/1962 | Graham ................................ 378/58 |
| 3,614,427 | 10/1971 | Vacher ................................ 378/189 |
| 3,673,407 | 6/1972 | Wiswell, Jr. ........................ 378/58 |
| 3,829,699 | 8/1974 | Anspach, Jr. . |
| 3,891,845 | 6/1975 | English . |
| 3,993,906 | 11/1976 | English . |

Primary Examiner—Carolyn E. Fields
Assistant Examiner—Joseph A. Hynds
Attorney, Agent, or Firm—Seed and Berry

[57] ABSTRACT

A method and apparatus are disclosed for performing in-bath filming during extracorporeal shock wave lithotripsy. The device has a holder for slidably receiving a film cassette and a grid therein. The holder has means for slidably mounting the holder on the image intensifier portion of an x-ray fluoroscope so that forces on the front of the holder can be transferred to pressure sensing means on the intensifier. The holder is constructed in a water-tight manner so that the film contained in the holder may be delivered beneath the level of water in the bath adjacent the abdomen of the patient in the bath. An inflatable bladder is provided on the outside of the holder to displace water from the area between the holder and the abdomen to prevent absorption and scattering of the x-rays by water in the area between the holder and the patient's abdomen.

13 Claims, 4 Drawing Figures

METHOD AND APPARATUS FOR ESWL IN-BATH FILMING

DESCRIPTION

1. Technical Field

The invention relates to methods and apparatus for making x-ray films. More specifically, the invention relates to a method and apparatus forming x-ray images during extracorporeal shock wave lithotripsy.

2. Background of The Art

The recent development of extracorporeal shock wave lithotripsy (ESWL) has greatly reduced the necessity for performing surgery to remove calculi from renal tissue. The occurrence of calculi in tissue frequently occurs in the form of what is commonly known as kidney stones. ESWL has provided a method for fragmenting the calculi with pressure waves so that the stones may be passed in urine without resort to surgery in the majority of cases.

During ESWL treatment the patient is immersed and stabilized in a tub filled with demineralized and degassed warm water. Pressure waves are transmitted through the water and focused on the calculi to pulverize the calculi into particles having the size of sand grains. x-ray fluoroscopes are used to aim the electrodes which generate the pressure waves in the water bath. Typically, the x-ray sources are placed beneath the tub while the fluoroscope image intensifiers are placed in direct contact with the abdomen of the patient at the axial position of the x-ray image. Video monitors provide a picture of the calculi which allows the focus of the pressure waves to be precisely positioned. A forward head portion of the image intensifier penetrates the top level of the water and touches the abdomen of the patient.

Although this procedure has been highly effective for reducing the need for surgery it has been found that the images provided by the fluoroscopes (two fluoroscopes are usually provided to get more precise positioning of the shock waves) have insufficient resolution to provide good aiming of the shock wave generator electrodes once the calculi has been broken down into smaller fragments. Moreover, the resolution is insufficient to access the size of the calculi fragments and whether further exposure to the shock waves is necessary. Presently patients are removed from the water bath after the initial treatment and taken to an x-ray facility to provide high resolution x-ray images of the treated tissue. If further treatment is required, the patient is then reinserted into the water bath and again immobilized therein. The fluoroscope images are compared to the x-ray images so that the shock waves can be precisely focused on the remaining particles.

This procedure is extremely inefficient and expensive and results in under utilization of the machines. Presently, cost of these machines are on the order of $1.7 million dollars. Moreover, patients receive more shocks than would be necessary if the location and size of the fragments could be more precisely determined without removing the patient from the bath. Thus, a need exists for producing high resolution images during ESWL which does not require removal of the patient from the water bath. Furthermore, more precise aiming of the electrode pressure wave generators could reduce the number of shocks which a patient would have to receive thereby decreasing hematuria and renal morbidity (blood in the urine and kidney tissue damage).

DISCLOSURE OF THE INVENTION

It is therefore an object of the invention to provide a method and apparatus for producing in-bath x-ray films to provide a high resolution x-ray image of the treated area without removing the patient from the water bath.

Basically, the invention achieves this object and other objects and advantages which will become apparent from the description below by providing a x-ray film cassette holder which is mountable on the image intensifier portion of an x-ray fluoroscope. The film holder is provided with means for displacing water between the film holder and the patient's abdomen so that absorption and scattering of the x-rays by water is minimized.

In the preferred embodiment, the holder is slidably mounted on the end of the intensifier so that the intensifier may be driven towards the patient's abdomen in the conventional manner by an electric motor without defeating the pressure sensing feature of such intensifiers which cuts off the electric drive once the end of the intensifier has contacted the abdomen. In this way, the sliding feature of the holder transfers pressure from the contact between the patient's abdomen and the holder to the extending portion of the intensifier to activate the pressure sensitive switch. The holder incorporates means for maintaining a film cassette and a grid in a proper orientation to the x-rays and in a water-tight environment so that the film and grid can be immersed beneath the level of the water in the bath.

The invention is most advantageous in that high resolution x-ray films can be produced without removing the patient from the water thereby improving the accuracy and efficiency of the treatment and decreasing undesirable side effects.

BEST MODE FOR CARRYING OUT THE INVENTION

Figures 1, 2:
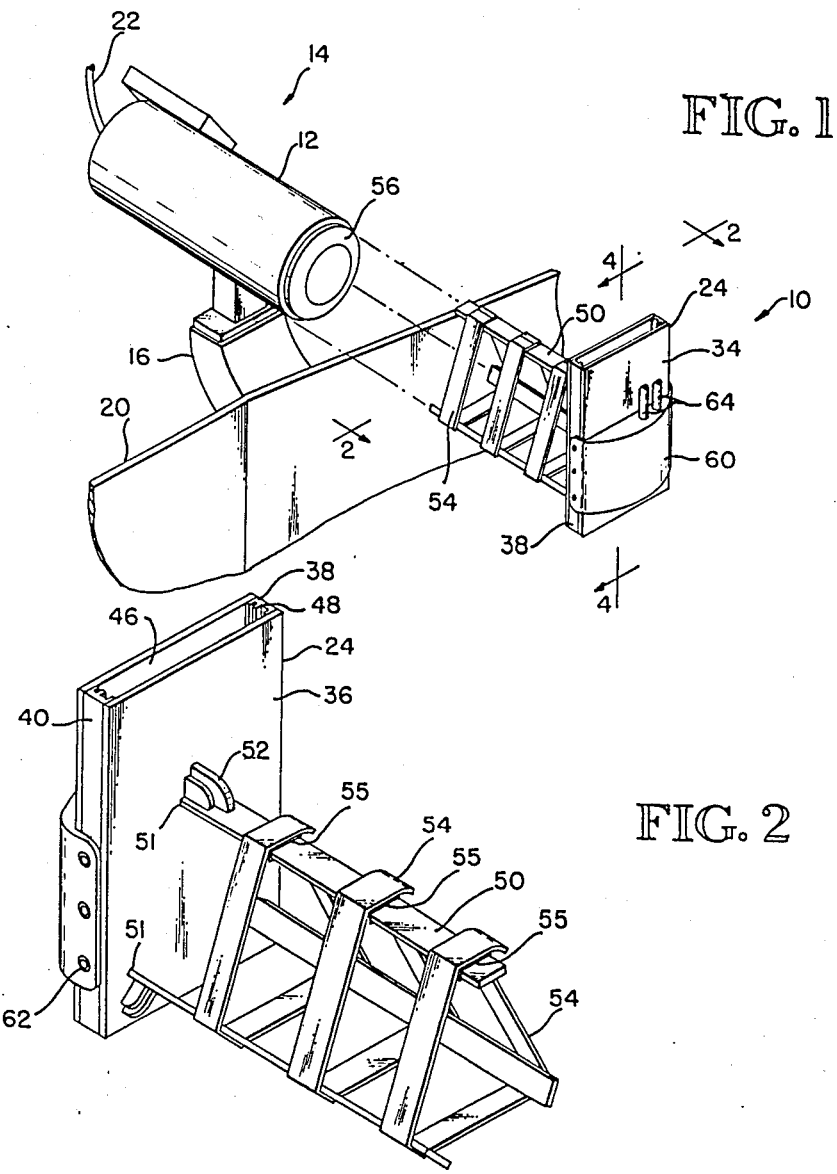
FIG. 1 is an isometric view of a portion of a water bath wall, a conventional fluoroscope image intensifier and the fluoroscope attachment of the present invention.
FIG. 2 is an enlarged isometric view of the holder of FIG. 1 looking generally in the direction of arrows 2—2 of FIG. 1.
Figure 3:
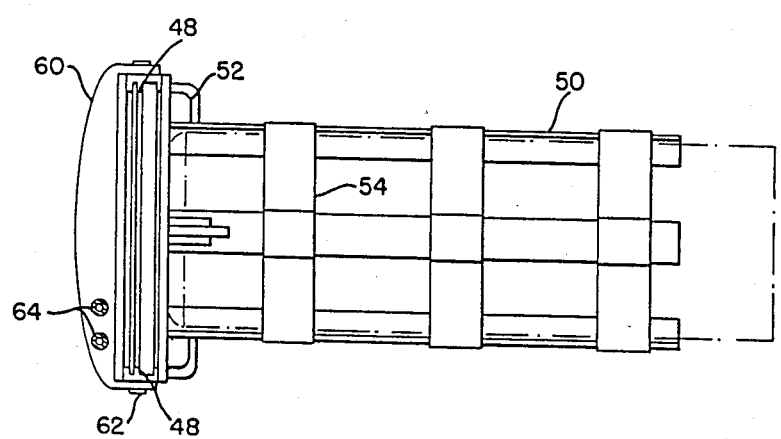
FIG. 3 is a top plan view of the fluoroscope attachment of FIG. 1.

In FIG. 1, a fluoroscope attachment for holding a grid and film cassette for in-bath filming during extracorporeal shock wave lithotripsy (ESWL) is generally indicated by reference numeral 10. The attachment is slidably mountable to the outer housing 12 of an image intensifier 14 of a fluoroscope. The image intensifier 14 is connected by an arm 16 to a sidewall portion 20 of an immersion tub for ESWL treatment. The remainder of the ESWL machine is not shown but is entirely conventional and well known by those skilled in the art.

The image intensifier 14 of the fluoroscope illustrated in FIG. 1 is from a Dornier ESWL manufactured by Dornier System GmbH, Friedrichafen, West Germany. In this instrument, the patient is submerged in a demineralized water bath and immobilized in the bath using a suspended chair arrangement (not shown). The patient is strapped into the chair so that the kidneys can be precisely located while in the bath. Underwater electrodes (not shown) produce pressure waves which pass through the water and the patient's soft tissue until calculi (kidney stones) are encountered. The calculi absorb the energy transmitted by the waves and shatter due to the brittle nature of the calculi. After repeated shock waves (up to 2000) sufficient fragmentation of the calculi occurs so that the fragments may be passed through the urine.

The image intensifier 14 transmits a video signal through a cable 22 to a video monitor (not shown). In the conventional machine as manufactured, the image on the monitor is used to focus the pressure waves on the calculi. The fluoroscopic image produced on the video monitor, however, has insufficient resolution to allow accurate aiming of the shock waves once the calculi has been broken up into smaller fragments. Moreover, the resolution is insufficient to access the size of the calculi fragments and whether further exposure to the shock waves is necessary. In the past, the patients have been typically removed from the water bath to an x-ray facility where x-ray films of the treated area are taken. The patient is then reinserted into the bath for further treatment. The physician compares the fluoroscopic images received by the image intensifier (two are typically provided to provide accurate focusing of the beam at a position defined by two axis) to the x-ray films to correctly identify the position of fragmented calculi for further fragmentation.

The fluoroscopic attachment 10 of the present invention provides an apparatus and method for producing high resolution x-ray films of the relevant abdominal area without removing the patient from the bath. A number of advantages accrue from such in-bath filming including reducing the number of shocks necessary for successful treatment, potentially decreasing renal morbidity, reducing the number of electrodes necessary per patient treatment, decreasing the time required for treatment, eliminating the preparation time otherwise necessary when the patient is reinserted in the bath for further treatment, and decreasing repeat ESWL treatment, all of which reduce the overall cost of the procedure. The method of in-bath filming which has been developed can be quickly and easily done during the procedure with a total required time of only about three to five minutes. The quality of the film obtained is excellent and allows determination of the completeness of fragmentation. The quality of x-ray images obtained are superior to that attainable with the currently available multi-format images recorded from the video monitors.

Figure 4:
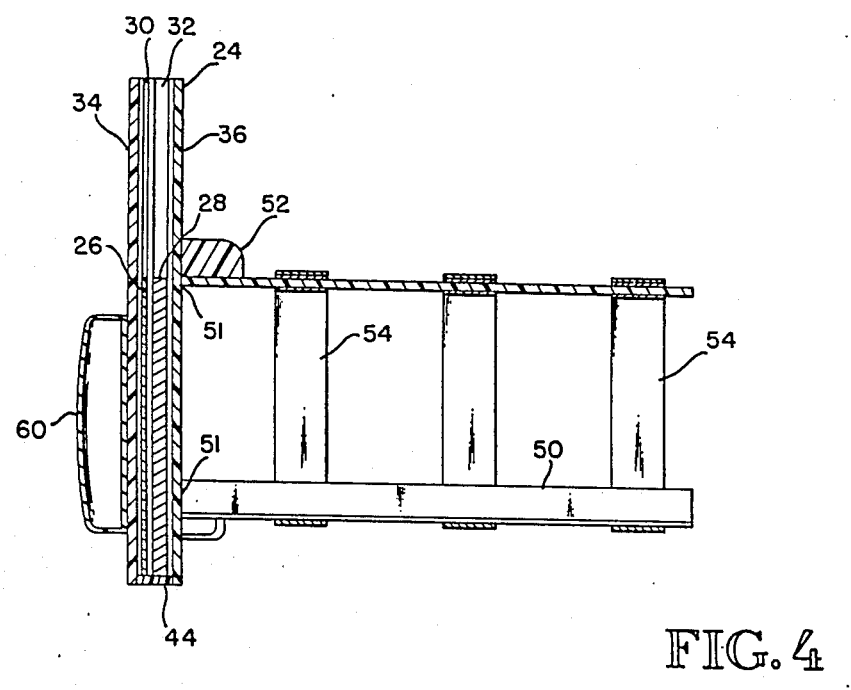
FIG. 4 is a sectional view taken generally along lines 4—4 of FIG. 1.

As shown in the remaining figures, the fluoroscope attachment 10 has a holder 24 which is adapted to receive a grid 26 (80 cm focus, 8:1, 34 lines per centimeter) and a 24×24 centimeter film cassette 28 with Lanex regular screens and OG film (Kodak Company). The grid and film cassette are shown in FIG. 4 removably positioned in a grid receptacle 30 and a film receptacle 32, of the holder 24. The holder 24 has a front wall 34 constructed from a substantially x-ray transparent plate material which is maintained in a spaced apart substantially parallel relation from a similarly x-ray transparent back wall 36. The holder has left and right sidewalls 38 and 40, respectively, and a bottom 44. The front wall, back wall, sidewalls, and bottom are constructed of a waterproof material and define a watertight container with an open upper end. The receptacles 30 and 32 formed within the holder 24 are defined by the front and back walls, sidewall and bottom, and have an open upper end sized to accept the film cassette and grid therethrough. Projections 48 extend inwardly from the sidewalls to further define the grid and film receptacles 30 and 32, and hold the grid and film in proper position within the holder relative to each other.

Attach means are provided for slidably mounting the holder 24 to the outer housing 12 of the image intensifier 14. It is noted that the outer housing is manufactured from a waterproof material and provides a seal to prevent the invasion of water into the interior of the image intensifier. The attachment means provided hold the film cassette substantially perpendicular to the longitudinal axis of the image intensifier 14, and hence substantially perpendicular to the axis of the x-ray beam impinging upon the film cassette 28. Of course, this orientation is parallel to the x-ray image focused on the intensifier. As such, an undistorted image is produced on the x-ray film.

In the preferred embodiment of the invention the attachment means are three struts 50 which extend rearwardly from the back wall 36 of the holder 24 with a substantially perpendicular relationship thereto. As shown in the figures, the three struts are circumferentially and radially spaced apart from one another sufficiently to closely accept the cylindrical outer housing 12 of the image intensifier 14 therebetween but allow the fluorscope attachment 10 to slidably move longitudinally relative to the image intensifier.

The struts 50 are fixedly attached to the back wall 36 and reinforcing members 52 are provided at the ends 51 of each strut connected to the back wall to maintain the perpendicular relationship between the back wall and the struts. As such, the struts hold the holder 24 and hence the film assette 28 properly oriented with respect to the x-ray beam. Moreover, no fixed attachment to the image intensifier is required and the waterproof outer housing of the image intensifier need not be pierced. Since the front and back walls 34 and 36 are x-ray transparent, and the holder 24 does not otherwise affect the functioning of the intensifier, the intensifier may be easily and quickly utilized in a conventional fashion without removal of the attachment 10 if only the film cassette 28 and grid 26 are removed from the holder 24.

Three straps 54 have their one end fixedly connected to one of the struts at three distant positions. The straps may be wrapped around the outsides of the struts 50 after the image intensifier 14 has been placed within the space defined by the struts. Velcro TM strips 55 are provided on the outer side of the strap ends connected to each strut. This allows the straps to be wrapped around the struts to slidably secure the struts to the outer housing 12 of the image intensifier 14 and to interconnect the struts to maintain their circumferential position about the housing. The strap can be tightened as desired to vary the degree of ease with which the struts can slidably move relative to the outer housing.

The image intensifier shown has a forwardly head portion 56 which projects forward from the outer housing 12 of the intensifier. When the image intensifier is used without the fluoroscope attachment 10, the image intensifier is moved toward the patient to place the head portion 56 into contact with the abdomen of a patient in the water bath by a motor (not shown). A pressure sensor internal to the head portion detects contact of the head portion with the patient's abdomen, and a switch operatively connected to the pressure sensor stops the motor when the contact pressure achieves a predetermined value. With the present invention, the strut and strap arrangement allows the fluorscope attachment 10 to slidably engage the outer housing 12 so that the holder 24 will not prevent operation of the pressure sensor as the image intensifier is moved to position the holder 24 at the abdomen of the patient. In this way the pressure sensor and switch within the head portion remain operative while the attachment is on the outer housing 12. That is, when the attachment comes into contact with the patient's abdomen with sufficient contact pressure the motor drive for the image intensifier will stop.

An inflatable bladder 60 is attached to the front wall 34 of the holder 24 by fasteners 62. Any suitable method may, of course, be chosen for attaching the bladder 60 to the front wall of the holder. The bladder preferably covers an area sufficiently large that when inflated and positioned against the patient the x-rays necessary to expose the film in the film cassette, which is held in the film receptacle 32, will not have to pass through the water bath where high absorption and scattering occur. Rather, the water is displaced by the inflated bladder and the x-rays pass through the inflated bladder with minimal absorption or scattering resulting. The bladder is inflated prior to an exposure of the film after the holder 24 has been moved into close proximitiy to the patient's abdomen. Conventional air tubes 64 are provided to allow inflation and deflation of the bladder. Two tubes 64 may be provided as shown for inflating and deflating the bladder, or a single tube may be used provided appropriate check valves are incorporated in the tubing.

The bladder 60 is inflated to displace water from the area between the front wall of the holder 24 and abdomen of the patient. The bladder is flexible to conform to the irregular shapes of patient's abdomen areas into which it contacts to more fully displace the water. It is well known that water tends to absorb and scatter x-rays which would be detrimental to the formation of a high resolution x-ray film. The means for inflating an deflating the bladder are not shown but may include any conventional means such that used with conventional sphgmomanometer cuffs. In a preliminary embodiment it was found that the inflatable rubber balloon from a large sphgomomanometer was effective for use as the inflatable bladder 60.

When it is desired to more precisely locate the position of fragmented calculi in the kidneys or other abdominal region, the following procedure is followed. The head struts 50 of the attachment are slidably secured to the outer housing 12 by appropriate tensioning of the straps 54. The image intensifier 14 is then moved toward the patient until the holder 24 is positioned adjacent to the the abdomen of a patient in the water bath. It is noted that if the motor drive causes the image intensifier to push the holder 24 too hard against the patient, the back-wall 36 of the holder will bear on the internal pressure sensor with sufficient force to switch off the motor since the struts 50 allow the fluoroscope attachment 10 to slide rearwardly.

The inflatable bladder 60 is then inflated to displace water from the area between the front wall 34 of the holder and the abdomen. When used with the Dornier ESWL device the integral x-ray portion (manufactured by Philips Co.) is adjusted for an x-ray exposure. This is done by turning off the image storage selectors in the image intensifier portion 14 and initiating an x-ray exposure technique by depressing the kilovolt-miliamperes button on the x-ray control panel. The kilovolt and miliampere settings can then be adjusted and the exposure made by depressing the exposure release button on the control handle. For an average size patient a setting of 65 kilovolts and 50 miliamperes is selected when using a grid and film cassette of the type previously described.

The correct inflation of the inflatable bladder 60 to displace all water is important to obtaining an x-ray film with maximum resolution. With thinner patients this is especially a problem since there tends to be large gaps between the substantially planar front wall 34 of the holder 24 and the curved surface of the abdomen. To the extent that water is not displaced from the space between the front wall in the abdomen a reduction in image resolution will occur. With heavier patients the problem does not tend to be as acute, however, care should nonetheless be used to insure that the bladder is sufficiently inflated.

In the preferred embodiment the holder 24 has a vertical height of approximately 18 inches and a horizontal width of approximately 11 inches. The outside depth dimension of the holder and therefore the sidewalls, and bottom is approximately 2 inches. The film receptacle 32, defined by the back wall and projection 48, has a width of approximately ⅝ of an inch to slidably accept a film cassette 28 of the type described. The grid receptacle 30 is positioned forwardly of the film receptacle and held separated therefrom by the projection 48 and has a preferred width of approximately ⅛ of an inch to slidably receive a grid 26 of the type described. The struts 50 have a length of approximately 19 inches.

As will be readily apparent to one skilled in the art, the dimensions cited above are illustrative of a preferred embodiment only and may be varied so long as the primary functions of the various parts of the fluoroscope attachment 10 are not impaired. For example, the struts 50 may be lengthened or shortened according to the dimensions of the image intensifier upon which the attachment is to be mounted. Furthermore, four or more struts may be provided instead of the three specified in the preferred embodiment. Further yet, the struts may be altogether substituted for by a more dedicated structure which more closely corresponds to the structure of the image intensifier housing 12. Other means for mounting the holder 24 to the image intensifier 14 which do not include the use of struts are considered to be part of the invention. Specifically, clamps with extending members or dedicated housings adapted to receive the outer portion of the image intensifier are contemplated.

Therefore, the scope of the invention is not to be limited by the above description but it is to be determined by the claims which follow.

We claim:

1. A fluoroscope attachment for holding a grid and film cassette for in-bath filming of a patient exposed to an x-ray beam generated by an x-ray source and received by a motor drive fluoroscope image intensifier having pressure sensing means to stop the motor drive, the attachment being usable during extracorporeal shock wave lithotripsy in which the patient to be filmed is submerged in a water bath, comprising:

a holder having a substantially x-ray transparent front wall and a back wall spaced rearwardly from the front wall and having two sidewalls and a bottom connected to the front and back walls in a fluid-tight relation so as to form a receptacle with an open top to accept a film cassette and a grid, wherein the sidewalls have means for holding the film cassette and the grid in a spaced parallel relation within the receptacle;

means for slidably mounting the holder to the outer housing of the image intensifier so that a film cassette and grid in the holder are positioned substantially perpendicular to the x-ray beam incident on the image intensifier and so that the holder can slide on the intensifier to allow the back wall to transfer force to the intensifier pressure sensing means; and a resilient water displacing member attached to the outside of the front wall and covering an area at least as large as the area of the beam incident on a film cassette in the holder to displace water from the area between the front wall of the holder and a patient in the water bath.

2. The attachment of claim 1 wherein the mounting means comprises at least three elongated struts rearwardly extending from and attached to the back wall of the holder and oriented to hold the film cassette in the holder substantially perpendicular to the x-ray beam, wherein the struts are spaced apart to slidably receive therebetween and frictionally engage the outer housing of the fluorscope image intensifier.

3. The attachment of claim 2 including means for tightening the struts against the outer housing of the fluoroscope image intensifier to adjust the frictional sliding engagement of the struts with the housing and for maintaining the relative positions of the struts on the housing.

4. The attachment of claim 3 wherein the tightening means comprises straps transversely extendable about the struts and connected to at least one strut.

5. The attachment of claim 2 wherein the back wall is parallel to the front wall and the attachment further includes means for reinforcing the attachment of the struts to the back wall to maintain the perpendicular position of a film cassette in the holder to the x-ray beam.

6. A fluoroscope attachment for in-bath filming of a patient in a water bath during fluoroscopic monitoring by x-ray beam in extracorporeal shock wave lithotripsy, comprising:

a watertight film holder having an open top and means for holding a film cassette therein;

means for mounting the holder to a fluoroscope image intensifier wherein a film cassette in the holder is oriented substantially perpendicular to the x-ray beam; and means for displacing water from the area between the holder and the patient in the water bath, said displacement means being positioned on the outside of the holder.

7. The attachment of claim 6 for use with a fluoroscope image intensifier having pressure sensing means wherein the mounting means slidably engages the image intensifier so that forces on the holder are transferred to the image intensifier pressure sensing means.

8. A method for in-bath filming during extracorporeal shock wave lithotripsy, comprising the following steps:
placing a film cassette in a watertight holder;
slidably mounting the holder to a fluoroscope image intensifier with the film cassette oriented substantially perpendicular to the x-ray beam;
moving the image intensifier to position the holder in the water bath with the holder in close proximity to the patient in the water;
inflating a bladder positioned between the holder and the patient so as to displace water in the space therebetween; and
exposing the film cassette with an x-ray source so as to pass the x-ray through the patient and the holder and onto the film cassette contained in the holder.

9. A fluoroscope attachment for holding a grid and film cassette for in-bath filming of a patient exposed to an x-ray beam generated by an x-ray source and received by a motor driven fluorscope image intensifier having pressure sensing means to stop the motor drive, the attachment being usable during extracorporeal shock wave lithotripsy in which the patient to be filmed is submerged in a water bath, comprising:

a holder having a substantially x-ray transparent front wall and a back wall spaced rearwardly from the front wall and having two sidewalls and a bottom connected to the front and back walls in a fluidtight relation so as to form a receptacle with an open top to accept a film cassette and a grid, wherein the sidewalls have means for holding the film cassette and the grid in a spaced parallel relation within the receptacle; and means for slidably mounting the holder to the outer housing of the image intensifier so that a film cassette and grid in the holder are positioned substantially perpendicular to the x-ray beam incident on the image intensifier and so that the holder can slide on the intensifier to allow the back wall to transfer force to the intensifier pressure sensing means.

10. The attachment of claim 9 wherein the mounting means comprises at least three elongated struts rearwardly extending from and attached to the back wall of the holder and oriented to hold the film cassette in the holder substantially perpendicular to the x-ray beam, wherein the struts are spaced apart to slidably receive therebetween and frictionally engage the outer housing of the fluoroscope image intensifier.

11. A fluoroscope attachment for in-bath filming of a patient in a water bath during fluoroscopic monitoring by x-ray beam in extracorporeal shock wave lithotripsy, comprising:

a watertight film holder having an open top and means for holding a film cassette therein; and means for mounting the holder to a fluoroscope image intensifier wherein a film cassette in the holder is oriented substantially perpendicular to the x-ray beam.

12. The attachment of claim 11 for use with a fluoroscope image intensifier having pressure sensing means wherein the mounting means slidably engages the image intensifier so that forces on the holder are transferred to the image intensifier pressure sensing means.

13. A method for in-bath filming during extracorporeal shock wave lithotripsy, comprising the following steps:
placing a film cassette in a watertight holder;
slidably mounting the holder to a fluoroscope image intensifier with the film cassette oriented substantially perpendicular to the x-ray beam;
moving the image intensifier to position the holder in the water bath with the holder in close proximity to the patient in the water; and
exposing the film cassette with an x-ray source so as to pass the x-ray through the patient and the holder and onto the film cassette contained in the holder.

* * * * *

UNITED STATES PATENT AND TRADEMARK OFFICE
CERTIFICATE OF CORRECTION

PATENT NO. : 4,665,543
DATED : May 12, 1987
INVENTOR(S) : John F. Eusek, William H. Bush It is certified that error appears in the above—identified patent and that said Letters Patent is hereby corrected as shown below:

In claim 1, line 4, after the word "motor" delete the word "drive" and substitute therefor the word --driven--.

Signed and Sealed this

Twenty-seventh Day of October, 1987

Attest:

DONALD J. QUIGG

Attesting Officer

Commissioner of Patents and Trademarks